United States Patent
Herold et al.

(10) Patent No.: US 9,254,343 B2
(45) Date of Patent: Feb. 9, 2016

(54) METHOD AND DEVICE FOR STERILIZING PREFORMS

(75) Inventors: Thomas Herold, Ahrensburg (DE); Harald Rieger, Hamburg (DE); Dieter Klatt, Hamburg (DE); Frank Haesendonckx, Hamburg (DE)

(73) Assignees: KHS CORPOPLAST GMBH, Hamburg (DE); KHS GMBH, Dortmund (DE)

( * ) Notice: Subject to any disclaimer, the term of this patent is extended or adjusted under 35 U.S.C. 154(b) by 174 days.

(21) Appl. No.: 13/811,424

(22) PCT Filed: Jul. 18, 2011

(86) PCT No.: PCT/DE2011/001486
§ 371 (c)(1),
(2), (4) Date: Apr. 4, 2013

(87) PCT Pub. No.: WO2012/010166
PCT Pub. Date: Jan. 26, 2012

(65) Prior Publication Data
US 2013/0183195 A1     Jul. 18, 2013

(30) Foreign Application Priority Data
Jul. 22, 2010   (DE) .................. 10 2010 032 336

(51) Int. Cl.
*A61L 2/16*     (2006.01)
*A61L 2/20*     (2006.01)
(Continued)

(52) U.S. Cl.
CPC . *A61L 2/16* (2013.01); *A61L 2/208* (2013.01); *B29C 49/42* (2013.01); *B29C 49/46* (2013.01); *B29C 49/6409* (2013.01); *A61L 2202/23* (2013.01); *B29C 49/06* (2013.01); *B29C 49/12* (2013.01); *B29C 49/16* (2013.01);
(Continued)

(58) Field of Classification Search
CPC ........................................................ A61L 2/16
USPC .................................................. 422/28, 302
See application file for complete search history.

(56) References Cited

U.S. PATENT DOCUMENTS

| 4,076,071 A | 2/1978 | Rosenkranz et al. |
| 5,346,386 A | 9/1994 | Albrecht et al. |

(Continued)

FOREIGN PATENT DOCUMENTS

| CN | 101528271 A | 9/2009 |
| DE | 2352926 | 4/1975 |

(Continued)

OTHER PUBLICATIONS

English abstract for DE 102007050582 A1, inventor: Haesendonckx et al., publsihed: Apr. 30, 2009.*

*Primary Examiner* — Sean E Conley
(74) *Attorney, Agent, or Firm* — Lucas & Mercanti, LLP; Klaus P. Stoffel (57) ABSTRACT

The method and the device according to the invention are used to sterilize preforms (1) made of a thermoplastic material that are intended for producing blow-molded containers. During the sterilization, a sterilizing agent is introduced into the area of the preform (1). The sterilizing agent is discharged at least partially from at least one nozzle (44) in the direction of the preform (1). An average direction (45) of the escape of the sterilizing agent from the nozzle (44) is provided with an angle of inclination (46) from a longitudinal axis (47) of the preform (1).

12 Claims, 7 Drawing Sheets

(51) Int. Cl.
  *B29C 49/42* (2006.01)
  *B29C 49/46* (2006.01)
  *B29C 49/64* (2006.01)
  *B29C 49/06* (2006.01)
  *B29C 49/12* (2006.01)
  *B29C 49/16* (2006.01)
  *B29C 49/36* (2006.01)
  *B29K 23/00* (2006.01)
  *B29K 67/00* (2006.01)

(52) U.S. Cl.
  CPC ............ *B29C 49/36* (2013.01); *B29K 2023/12* (2013.01); *B29K 2067/00* (2013.01); *B29K 2623/12* (2013.01)

(56) References Cited

U.S. PATENT DOCUMENTS

| | | |
|---|---|---|
| 5,648,026 A | 7/1997 | Weiss |
| 6,692,684 B1 | 2/2004 | Nantin et al. |
| 7,160,509 B2 | 1/2007 | Masaoka |
| 7,900,422 B2 | 3/2011 | Fischer |
| 8,083,512 B2 * | 12/2011 | Adriansens ................ 425/174.4 |
| 8,092,757 B2 | 1/2012 | Adriansens et al. |
| 8,453,419 B2 | 6/2013 | Roithmeier |
| 8,470,240 B2 | 6/2013 | Quetel |
| 2008/0152538 A1 | 6/2008 | Quetel et al. |
| 2011/0061343 A1 | 3/2011 | Roithmeier et al. |
| 2011/0133370 A1 | 6/2011 | Engelhard et al. |
| 2011/0272861 A1 | 11/2011 | Humele |
| 2011/0285063 A1 * | 11/2011 | Chauvin et al. ............... 264/525 |

FOREIGN PATENT DOCUMENTS

| | | |
|---|---|---|
| DE | 4212583 | 10/1993 |
| DE | 4229580 | 3/1994 |
| DE | 4340291 | 6/1995 |
| DE | 19906438 | 8/2000 |
| DE | 10217145 | 10/2003 |
| DE | 102006053193 | 5/2008 |
| DE | 102007050582 | 4/2009 |
| DE | 102008056346 | 5/2010 |
| DE | 102009041215 | 3/2011 |
| EP | 1086019 | 9/2005 |
| EP | 1941913 Y | 7/2008 |
| EP | 1896245 | 5/2009 |
| EP | 2138298 | 12/2009 |
| EP | 2295324 | 3/2011 |
| FR | 2815542 A | 4/2002 |
| JP | H11321822 A | 11/1999 |
| JP | 200499111 A | 4/2004 |
| JP | 2008183899 A | 8/2008 |
| WO | 2009052800 | 4/2009 |
| WO | 2010020530 | 2/2010 |

* cited by examiner

METHOD AND DEVICE FOR STERILIZING PREFORMS

The present application is a 371 of International application PCT/DE2011/001486, filed Jul. 18, 2011, which claims priority of DE 10 2010 032 336.5, filed Jul. 22, 2010, the priority of these applications is hereby claimed and these applications are incorporated herein by reference.

BACKGROUND OF THE INVENTION

The invention concerns a method for sterilizing preforms that are made of a thermoplastic material and are intended for the production of blow-molded containers, in which a sterilizing agent is introduced into the area of the preform and in which the preforms are heated before they are blow molded.

In addition, the invention concerns a device for blow molding at least partly sterile containers by deforming a preform, said device having a delivery device for applying a sterilizing agent to at least part of the preform.

Finally, the invention concerns a device for sterilizing preforms that are made of a thermoplastic material and are intended for the production of blow-molded containers. The invention also comprises a device for producing at least partly sterile containers made of a thermoplastic material.

The invention also concerns a device for blow molding containers, which has at least one blowing station mounted on a support structure for blow molding thermoplastic preforms into containers.

Sterile blow-molded containers are typically produced by sterilizing the containers with hydrogen peroxide or other chemicals after they have been blow molded and before they are filled with a product. It is also well known that the preforms used as the starting product in the blow molding of the containers can be sterilized, especially the area of the inner surface of the preforms.

In container molding by the action of blowing pressure, preforms made of a thermoplastic material, for example, preforms made of PET (polyethylene terephthalate), are fed to different processing stations within a blow-molding machine. A blow-molding machine of this type typically has a heating system and a blowing system, in which the preform, which has first been brought to a desired temperature, is expanded by biaxial orientation to form a container. The expansion is effected by means of compressed air, which is fed into the preform to be expanded. DE-OS 43 40 291 explains the process-engineering sequence in this type of expansion of the preform.

The basic structure of a blowing station for container molding is described in DE-OS 42 12 583. Possible means of bringing the preforms to the desired temperature are explained in DE-OS 23 52 926.

Various handling devices can be used to convey the preforms and the blow-molded containers within the blow-molding device. The use of transport mandrels, onto which the preforms are slipped, has proven especially effective. However, the preforms can also be handled with other supporting devices. Other available designs are grippers for handling the preforms and expanding mandrels, which can be inserted in the mouth region of the preform to support the preform.

The handling of containers with the use of transfer wheels is described, for example, in DE-OS 199 06 438 with the transfer wheel arranged between a blowing wheel and a delivery line.

The above-explained handling of the preforms occurs, for one thing, in so-called two-step processes, in which the preforms are first produced by injection molding and temporarily stored and then later conditioned with respect to their temperature and blown into containers. For another, the preforms can be handled in so-called one-step processes, in which the preforms are first produced by injection molding and allowed to solidify sufficiently and are then immediately suitably conditioned with respect to their temperature and then blow molded.

With respect to the blowing stations that are used, various embodiments are known. In the case of blowing stations that are arranged on rotating transport wheels, book-like opening of the mold supports is often encountered. However, it is also possible to use mold supports that can be moved relative to each other or that are supported in a different way. In stationary blowing stations, which are suitable especially for accommodating several cavities for container molding, plates arranged parallel to one another are typically used as mold supports.

With respect to the sterilization of preforms, various prior-art methods and devices already exist, but they all have process-specific disadvantages that stand in the way of reliable sterilization of the preforms when high throughput rates are required at the same time.

EP 1 086 019 A, for example, describes the sterilization of hot preforms with a hot gaseous sterilizing agent. A succession of separate processing stations is used, namely, a first heating module, a sterilization module, and a second heating module. Disadvantages of this system are the temperature behavior of the preform during the sterilization process and the uncontrolled escape of the sterilizing agent from the preform within the heating stage.

EP 1 896 245 A describes a method in which a gaseous sterilizing agent is introduced into a cold preform and condensed therein before the preform is heated. A problem with this method is the difficulty of ensuring complete formation of condensate on the entire inner surface of the preform, since the hot sterilizing agent flowing into the preform raises the temperature of its inside wall. In addition, this method also allows uncontrolled escape of the sterilizing agent from the preform within the heating stage after it vaporizes in the heating zone.

EP 2 138 298 A describes a device in which, as a precautionary measure, sterilizing devices are arranged both upstream and downstream of the blowing module. This results in very high mechanical engineering expense.

WO 2010/020530 A1 describes the arrangement of a sterilization device between a heating device and the blowing module. In this method, the amount of sterilizing agent introduced into the area of the blowing module is difficult to predict. In addition, the amount of sterilizing agent released into the environment cannot be controlled, so that environmental contamination cannot be ruled out.

SUMMARY OF THE INVENTION

The objective of the present invention is to improve a method of the aforementioned type in such a way that sterilization can be carried out simply and reliably.

In accordance with the invention, this objective is achieved by virtue of the fact that the sterilizing agent is discharged at least partially from at least one nozzle in the direction of the preform, where a mean discharge direction of the sterilizing agent from the nozzle is provided with an angle of inclination to the longitudinal axis of the preform.

A further objective of the invention is to design a device of the aforementioned type in such a way that effective sterilization can be carried out with little expense.

In accordance with the invention, this objective is achieved by virtue of the fact that at least one nozzle for discharging the sterilizing agent has a mean discharge direction of the sterilizing agent such that this mean discharge direction has an angle of inclination with respect to the longitudinal axis of the preform.

The inclination of the mean discharge direction of the sterilizing agent relative to the longitudinal axis of the preform promotes the development of turbulent flow inside the preform and intensive contact between the sterilizing agent and the inner surface of the preform. The reference to the mean discharge direction of the fluid takes into consideration the fact that the fluid typically does not emerge from the nozzle with laminar flow but rather expands after it is discharged from the nozzle. This expansion is typically conical, at least in the vicinity of the nozzle.

Finally, a further objective of the present invention is to design a device of the aforementioned type for the blow molding of containers in such a way that the production of sterile containers is promoted.

In accordance with the invention, this objective is achieved by virtue of the fact that at least one nozzle for discharging the sterilizing agent has a mean discharge direction of the sterilizing agent that is inclined at an angle to the longitudinal axis of the preform.

An advantageous influence on the flow is realized if the angle of inclination is in the range of 10° to 80°.

In particular, it is proposed that the angle of inclination be in the range of 20° to 60°.

It has been found to be especially effective for the angle of inclination to be in the range of 30° to 35°.

Intensive contact of the sterilizing agent with the inside wall of the preform is promoted by virtue of the fact that the sterilizing agent flows from the nozzle into a mouth section of the preform.

It is also conducive to advantageous flow management if the outlet of the nozzle is positioned closer to an edge of the mouth section than to the longitudinal axis.

A simple design can be realized by conveying the preforms past a stationary sterilization device.

It is conducive to a continuous sequence of movement during the performance of the sterilization if the discharge zone of the nozzle is positioned some distance from an edge of the mouth section.

To achieve activation of the sterilizing agent, it is proposed that the temperature of the preform in the area of the inner surface be at least 80° C. while the sterilization is being carried out.

It has been found to be especially advantageous with respect to activation if the temperature is in the range of 100° C. to 130° C.

Specific embodiments of the invention are schematically illustrated in the drawings.

DETAILED DESCRIPTION OF THE INVENTION

Before explaining the detailed design of the device for sterilizing the preform 1 with the use of a sterilizing agent and before explaining the practical installation of a sterilization device in a blow-molding machine, we shall first describe the basic structure of a blow-molding machine.

Figure 1:
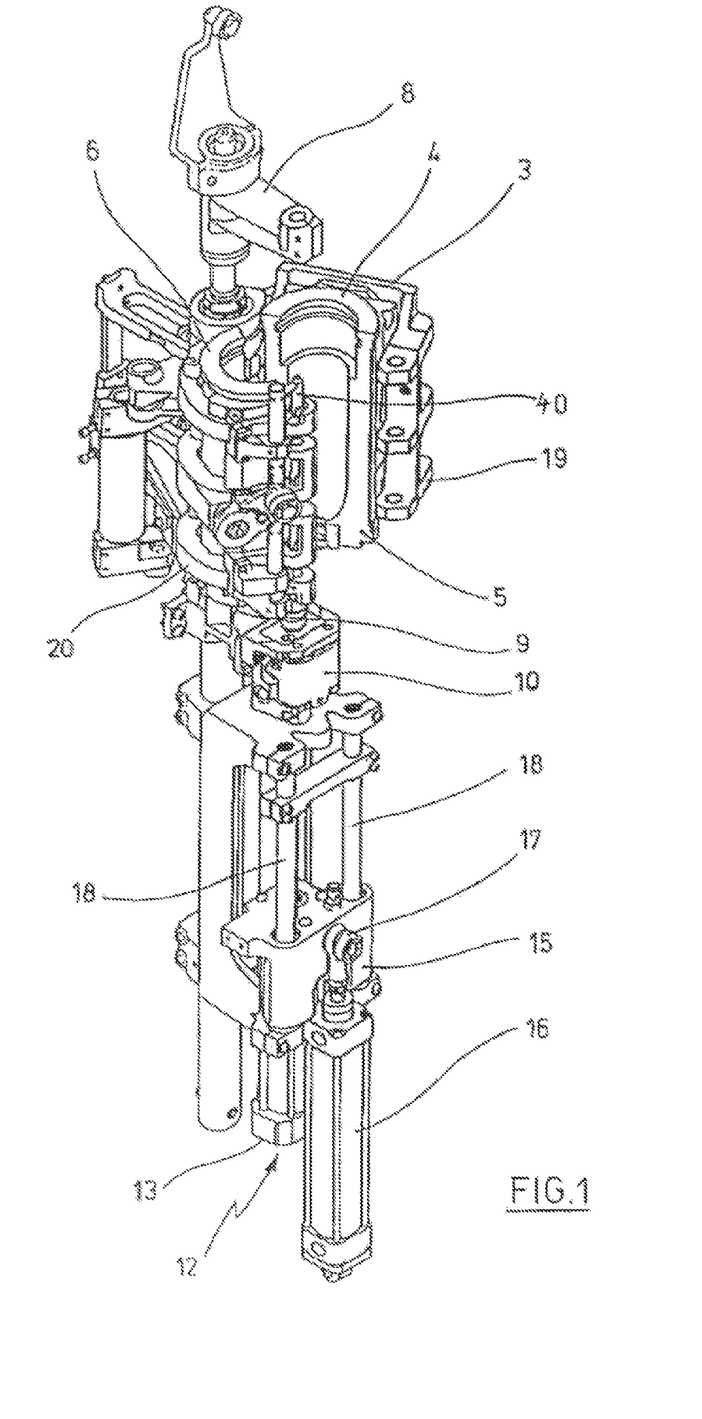
FIG. 1 shows a perspective view of a blowing station for producing containers from preforms.
Figure 2:
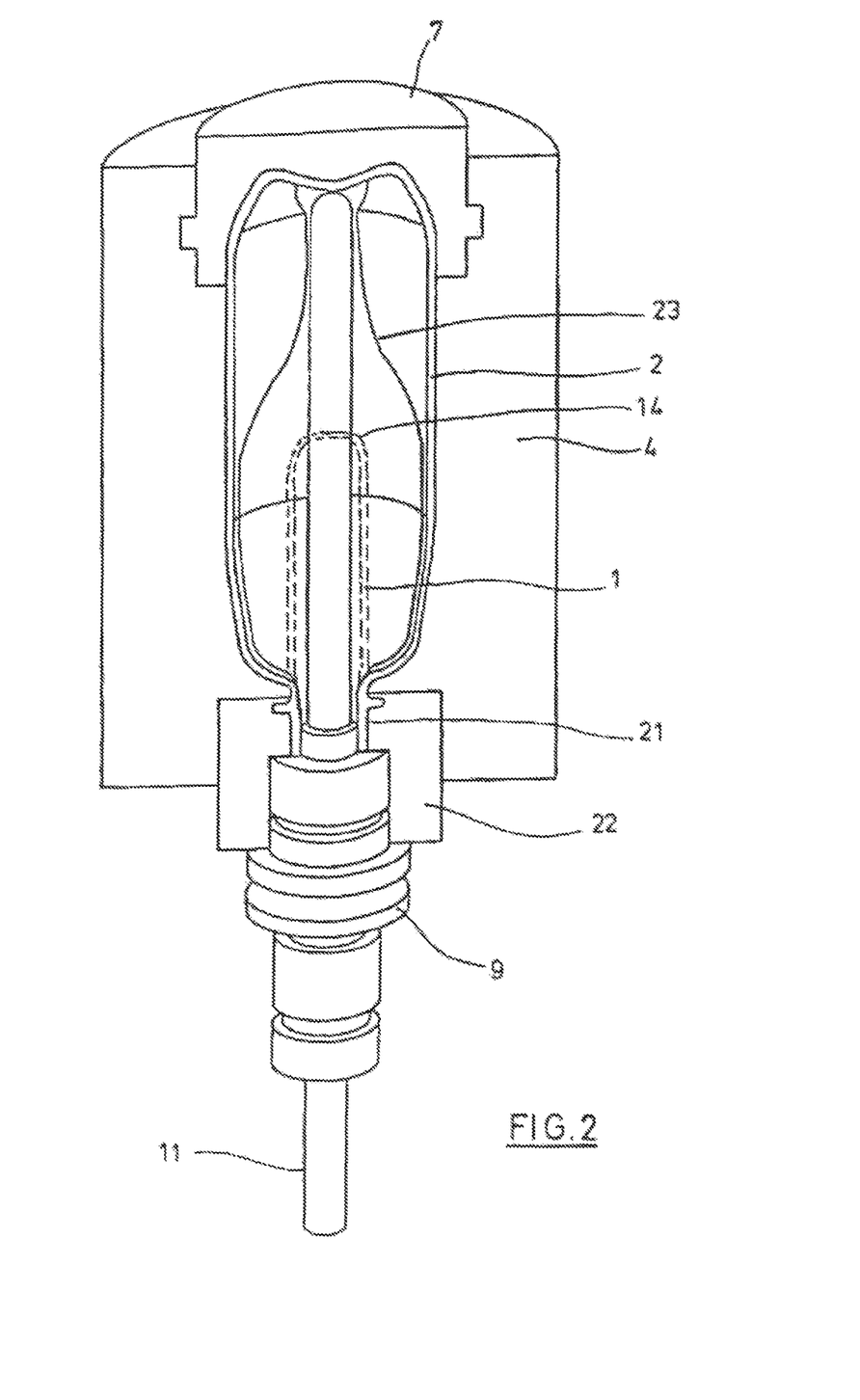
FIG. 2 shows a longitudinal section through a blow mold, in which a preform is stretched and expanded.

FIGS. 1 and 2 show the basic design of a device for shaping preforms 1 into containers 2.

The device for molding the container 2 consists essentially of a blowing station 3, which is provided with a blow mold 4, into which a preform 1 can be inserted. The preform 1 can be an injection-molded part made of polyethylene terephthalate. To allow a preform 1 to be inserted into the blow mold 4 and to allow the finished container 2 to be removed, the blow mold 4 consists of mold halves 5, 6 and a base part 7, which can be positioned by a lifting device 8. The preform 1 can be held in the area of the blowing station 3 by a transport mandrel 9, which, together with the preform 1, passes through a plurality of treatment stations within the device. However, it is also possible to insert the preform 1 directly into the blow mold 4, for example, with grippers or other handling devices.

To allow compressed air to be fed in, a connecting piston 10 is arranged below the transport mandrel 9. It supplies compressed air to the preform 1 and at the same time produces a seal relative to the transport mandrel 9. However, in a modified design, it is also basically possible to use stationary compressed air feed lines.

The preform 1 is stretched by means of a stretch rod 11, which is positioned by a cylinder 12. However, it is also basically possible for the stretch rod 11 to be mechanically positioned by cam segments, which are acted upon by pickup rollers. The use of cam segments is advantageous especially when a large number of blowing stations 3 is arranged on a rotating blowing wheel. The use of cylinders 12 is advantageous when stationary blowing stations 3 are provided.

In the embodiment illustrated in FIG. 1, the stretching system is designed in such a way that a tandem arrangement of two cylinders 12 is provided. Before the start of the actual stretching operation, the stretch rod 11 is first moved into the area of a base 14 of the preform 1 by a primary cylinder 13. During the stretching operation itself, the primary cylinder 13 with the stretch rod extended, together with a carriage 15 that carries the primary cylinder 13, is positioned by a secondary cylinder 16 or by a cam control mechanism. In particular, it is proposed that the secondary cylinder 16 be used in such a way under cam control that a current stretching position is predetermined by a guide roller 17, which slides along a cam track while the stretching operation is being carried out. The guide roller 17 is pressed against the guide track by the secondary cylinder 16. The carriage 15 slides along two guide elements 18.

After the mold halves 5, 6, which are arranged in the area of supports 19, 20, are closed, the supports 19, 20 are locked relative to each other by means of a locking mechanism 40.

To adapt to different shapes of a mouth section 21 of the preform 1, provision is made for the use of separate threaded inserts 22 in the area of the blow mold 4, as shown in FIG. 2.

In addition to the blow-molded container 2, FIG. 2 shows the preform 1, which is drawn with broken lines, and also shows schematically a container bubble 23 in the process of development.

Figure 3:
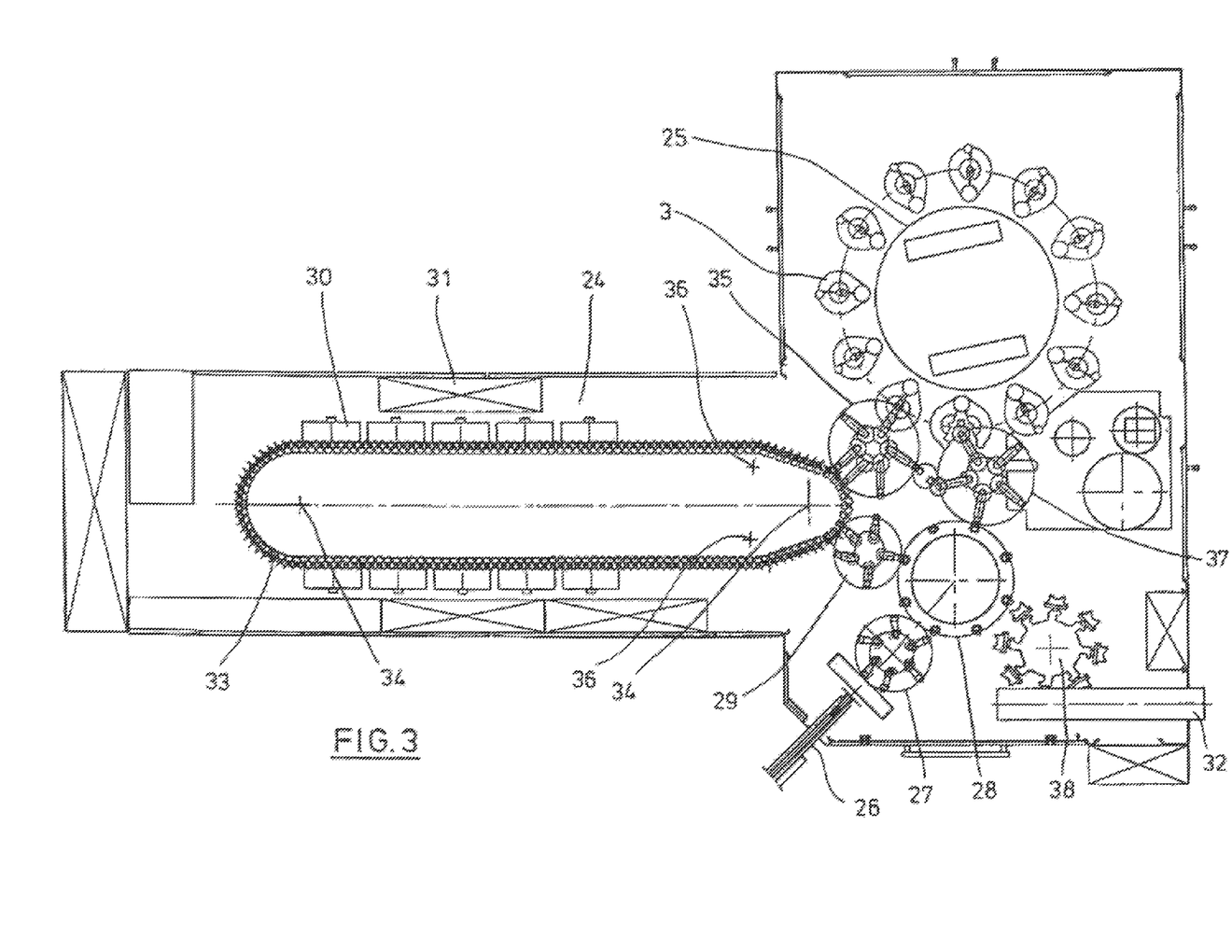
FIG. 3 is a drawing that illustrates a basic design of a device for blow molding containers.

FIG. 3 shows the basic design of a blow-molding machine, which has a heating line 24 and a rotating blowing wheel 25. Starting from a preform feeding device 26, the preforms 1 are conveyed to the area of the heating line 24 by transfer wheels 27, 28, 29. Radiant heaters 30 and fans 31 are arranged along the heating line 24 to bring the preforms 1 to the desired temperature. After sufficient heat treatment of the preforms 1, they are transferred to the blowing wheel 25, where the blowing stations 3 are located. The finished blow-molded containers 2 are fed to a delivery line 32 by additional transfer wheels.

To make it possible for a preform 1 to be formed into a container 2 in such a way that the container 2 has material properties that ensure a long shelf life of the foods, especially beverages, with which the container 2 is to be filled, specific process steps must be followed during the heating and orientation of the preforms 1. In addition, advantageous effects can be realized by following specific dimensioning specifications.

Various plastics can be used as the thermoplastic material, for example, PET, PEN, or PP.

The preform 1 is expanded during the orientation process by feeding compressed air into it. The operation of supplying compressed air is divided into a preblowing phase, in which gas, for example, compressed air, is supplied at a low pressure level, and a subsequent main blowing phase, in which gas is supplied at a higher pressure level. During the preblowing phase, compressed air with a pressure in the range of 10 bars to 25 bars is typically used, and during the main blowing phase, compressed air with a pressure in the range of 25 bars to 40 bars is supplied.

FIG. 3 also shows that in the illustrated embodiment, the heating line 24 consists of a large number of revolving transport elements 33, which are strung together like a chain and are moved along by guide wheels 34. In particular, it is proposed that an essentially rectangular basic contour be set up by the chain-like arrangement. In the illustrated embodiment, a single, relatively large-sized guide wheel 34 is used in the area of the extension of the heating line 24 facing the transfer wheel 29 and a feed wheel 35, and two relatively small-sized guide wheels 36 are used in the area of adjacent deflections. In principle, however, any other types of guides are also conceivable.

To allow the closest possible arrangement of the transfer wheel 29 and the feed wheel 35 relative to each other, the illustrated arrangement is found to be especially effective, since three guide wheels 34, 36 are positioned in the area of the corresponding extension of the heating line 24, namely, the smaller guide wheels 36 in the area of the transition to the linear stretches of the heating line 24 and the larger guide wheel 34 in the immediate area of transfer to the transfer wheel 29 and to the feed wheel 35. As an alternative to the use of chain-like transport elements 33, it is also possible, for example, to use a rotating heating wheel.

After the blow molding of the containers 2 has been completed, the containers 2 are carried out of the area of the blowing stations 3 by an extraction wheel 37 and conveyed to the delivery line 32 by the transfer wheel 28 and a delivery wheel 38.

Figure 4:
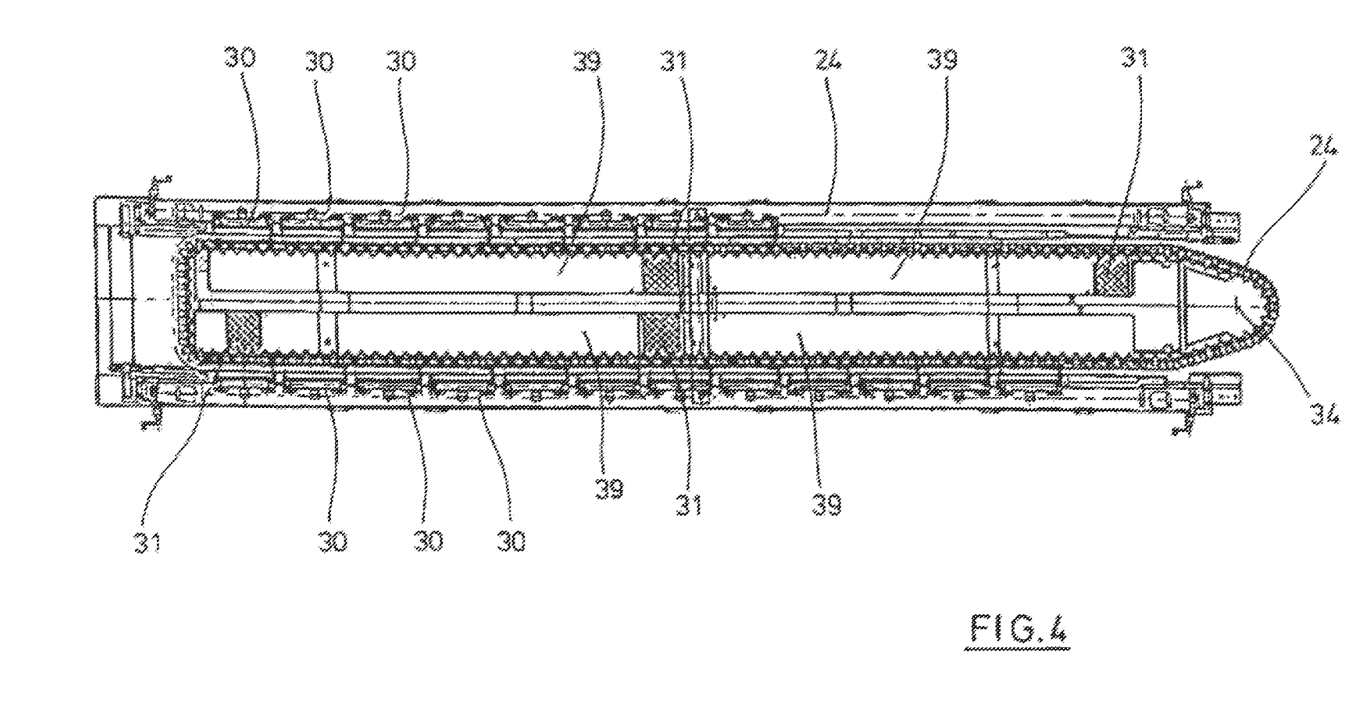
FIG. 4 shows a modified heating line with increased heating capacity.

In the modified heating line 24 illustrated in FIG. 4, a larger number of preforms 1 can be heated per unit time due to the larger number of radiant heaters 30. The fans 31 in this case feed cooling air into the area of cooling air ducts 39, which lie opposite the associated radiant heaters 30 and deliver the cooling air through discharge ports. A direction of flow of the cooling air essentially transverse to the direction of conveyance of the preforms 1 is realized by the arrangement of the discharge directions. In the area of surfaces opposite the radiant heaters 30, the cooling air ducts 39 can provide reflectors for the thermal radiation. It is also possible to realize cooling of the radiant heaters 30 by the delivered cooling air.

Figure 5:
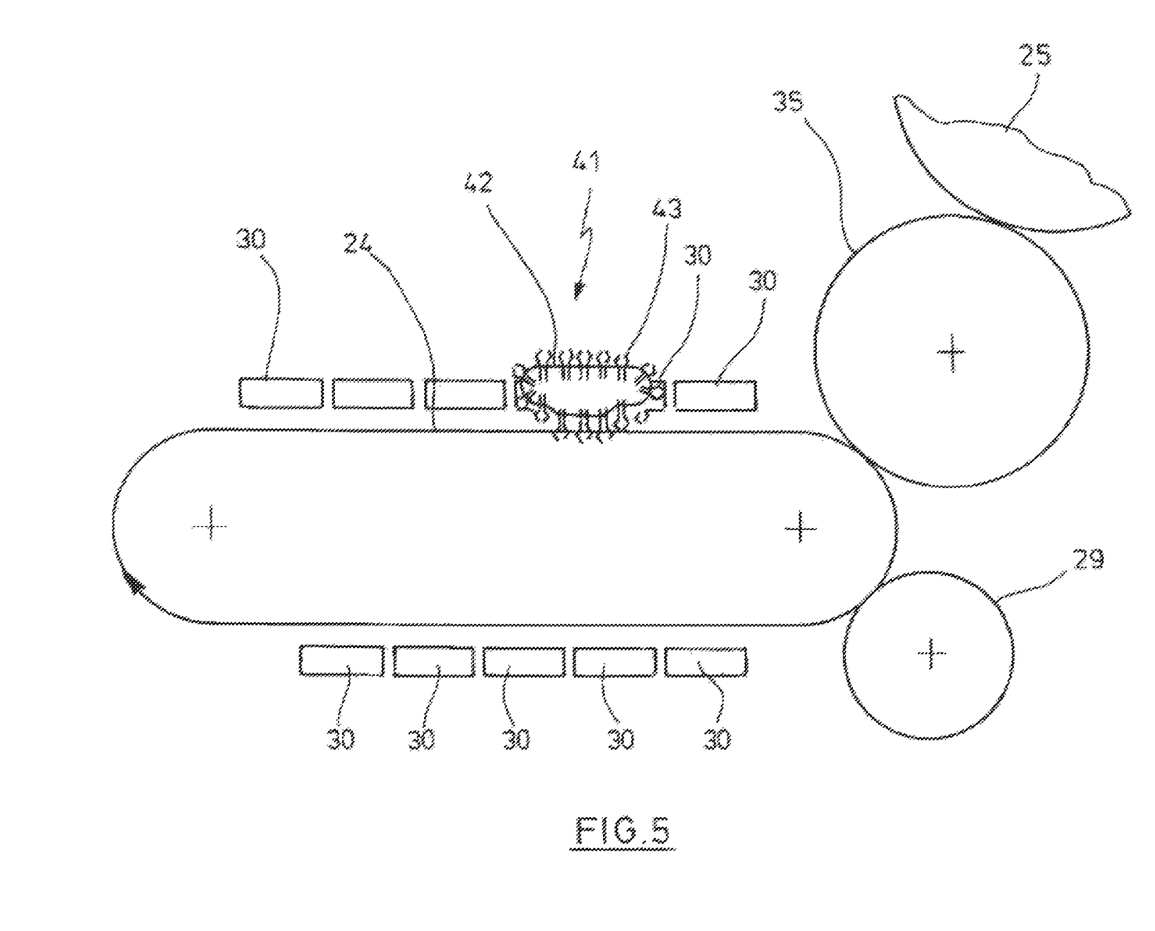
FIG. 5 is a schematic drawing of a heating module of a blow-molding machine, in which a sterilization device is arranged in the area of the heating module.

FIG. 5 is a schematic and greatly simplified drawing of a system similar to that shown in FIG. 3 with the additional installation of a sterilization device 41, which is shown here, by way of example, in the area of the heating line 24. In the embodiment illustrated in FIG. 5, a revolving conveyance system 42 for mounting elements 43 is arranged in the area of the sterilization device 41. The mounting elements 43 allow the preforms 1 to be held in place and/or positioned for at least part of the duration of the sterilization operation.

Figure 6:
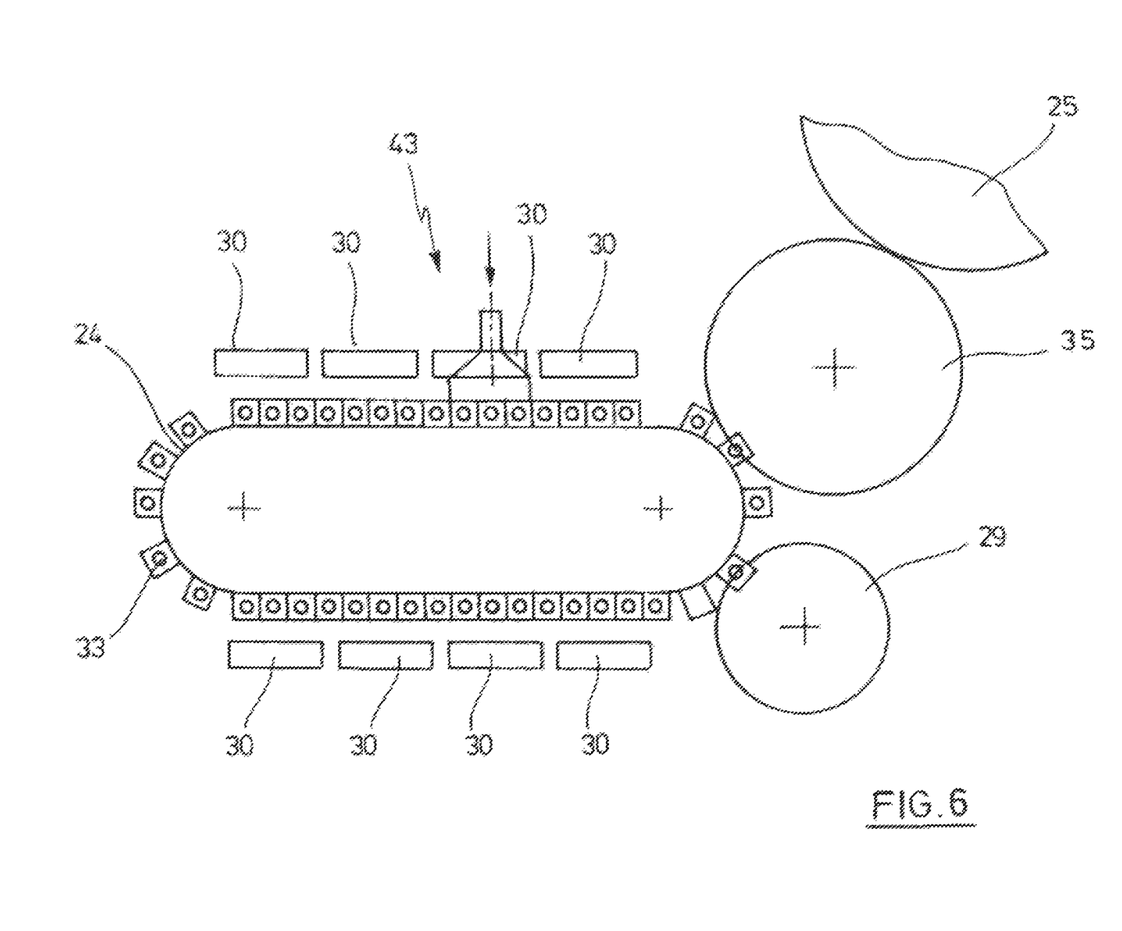
FIG. 6 is an embodiment that is modified relative to the embodiment of FIG. 5.

FIG. 6 shows a modified embodiment, in which additional mounting elements 42 are not used. Also shown in the drawing of FIG. 6 are the transport elements 33 of the heating line 24.

Figure 7:
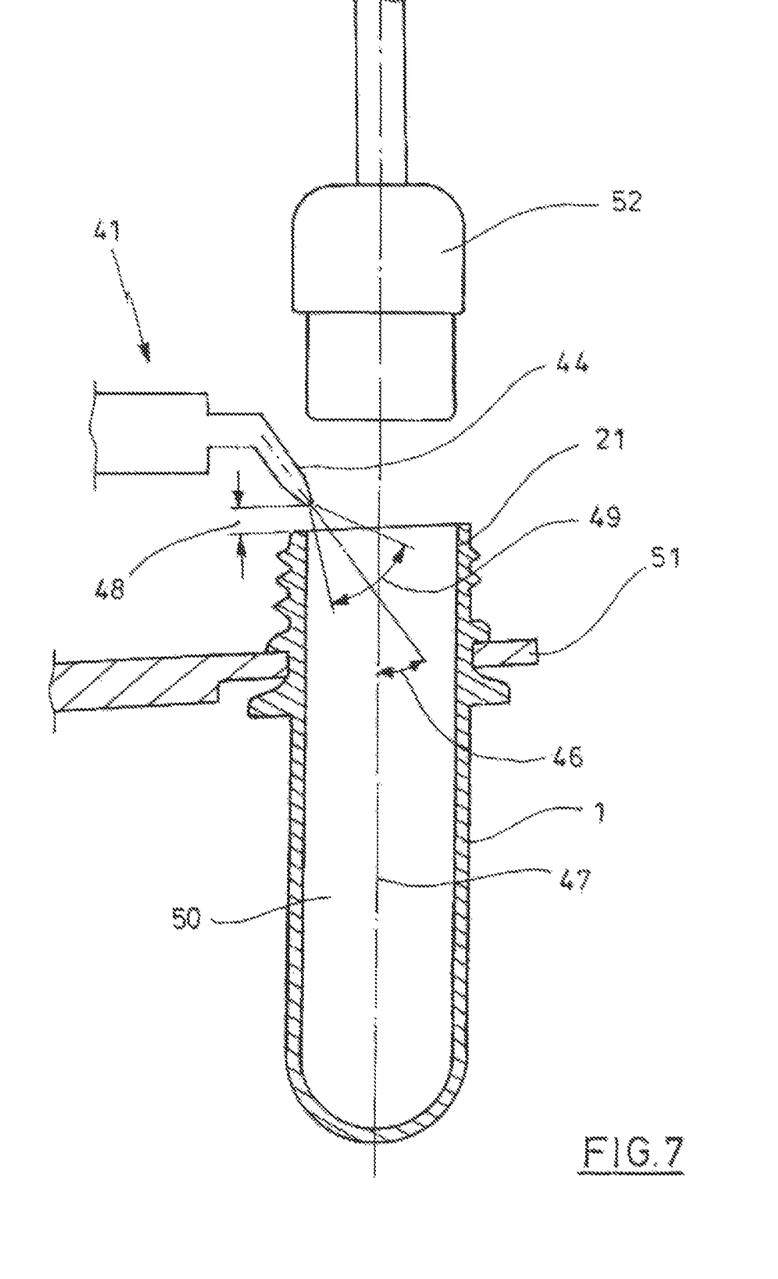
FIG. 7 is a schematic drawing of a longitudinal section through a preform with the associated nozzle for discharging a sterilizing agent.

In the embodiment shown in FIG. 7, the sterilization device 41 has a nozzle 44 for discharging the sterilizing agent. The nozzle 44 defines a mean discharge direction 45 of the sterilizing agent. The discharge direction 45 has an angle of inclination 46 to the longitudinal axis 47 of the preform 1. In the illustrated arrangement of the preform 1 with a longitudinal axis 47 oriented vertically, the angle of inclination 46 also corresponds to the angle between the discharge direction 45 and the vertical direction.

During the sterilization operation illustrated in FIG. 7, it is particularly proposed that the nozzle 44 be arranged in a stationary way and that the preform 1 be moved past the nozzle 44. In the illustrated embodiment with the preform 1 oriented with its mouth section 21 facing upward, it is especially advantageous if the nozzle 44 is positioned a small distance 48 above the mouth section 21. The sterilizing agent emerging from the nozzle 44 typically expands away from the nozzle at an angle of expansion 49.

It is also basically possible to arrange the nozzle in the interior space 50 of the preform 1 or to arrange the discharge region of the nozzle 44 flush with an edge of the preform 1. In the case of an arrangement of the preform 1 with its mouth section 21 oriented vertically downward, the arrangement according to FIG. 7 can be rotated 180°.

In the illustrated embodiment, the preform 1 is positioned by a mounting element 51 during the sterilization operation. The mounting element 51 can have a tong-like design. Before and after the sterilization operation is carried out, the preform 1 can also be positioned by a mounting element 52 that is inserted in the mouth section 21 or that surrounds the mouth section 21 like a bell. In this connection, the mounting element 52 is preferably clamped on the mouth section 21. The mounting element 52 preferably can be longitudinally positioned in the direction of the longitudinal axis 47.

The sterilizing agent is preferably introduced into the interior space 48 in a gaseous state. In particular, a temperature of the sterilizing agent above 100° C. is proposed. During the sterilization operation, the preform 1 preferably has a temperature above 80° C. in the area of its inner surface to be sterilized. It is proposed that especially hydrogen peroxide be used as the sterilizing agent.

In accordance with typical process conditions, the sterilizing agent has a temperature in the range of 100° C. to 130° C. during the sterilization operation. During the sterilization operation, the preform 1 has a temperature of 100° C. to 130° C., at least in the area of its inner surface. A typical sterilization time is about 0.1-0.5 s. The preferred sterilizing agent is vaporized hydrogen peroxide mixed with hot air. The concentration of hydrogen peroxide in this mixture is about 15-35% by weight.

In the specific embodiment shown in FIG. 7, the nozzle 44 has an inside diameter of 3.9 mm, and its discharge extends 56 mm in the mean discharge direction 45. The distance 48 is 10 mm in the illustrated embodiment.

The sterilizing agent is typically converted to the gaseous state at a vaporization temperature of 150° C. The aforementioned concentration of hydrogen peroxide corresponds to a content of about 0.05 to 0.5 kg $H_2O_2/Nm^3$.

In the case of stationary arrangement of the sterilization device 41 and conveyance of the preforms 1 past the sterilization device 41, it is especially proposed that the sterilizing agent be delivered continuously. Excess sterilizing agent or sterilizing agent emerging back out of the preform 1 can be removed by suction to prevent it from spreading out uncontrollably.

The invention claimed is:

1. A method for sterilizing preforms that are made of a thermoplastic material and are intended for producing blow-molded containers, the method comprising the steps of: introducing a chemical sterilizing agent into an area of the preform; and heating the preforms before they are blow molded, wherein the chemical sterilizing agent is discharged at least partially from at least one nozzle in a direction of the preform, where a mean discharge direction of the chemical sterilizing agent from the nozzle is provided with an angle of inclination to a longitudinal axis of the preform, wherein the preforms are conveyed past a stationary sterilization device in which the chemical sterilizing agent is introduced, wherein the preform is brought to a temperature of 80° C. before the chemical sterilizing agent is introduced so that the preform has the temperature of at least 80° C. in the area of the inner surface while the chemical sterilizing agent is being introduced.

2. The method in accordance with claim 1, wherein the temperature is in a range of 100° C. to 130° C.

3. The method in accordance with claim 1, wherein the angle of inclination is in a range of 10° to 80°.

4. The method in accordance with claim 3, wherein the angle of inclination is in a range of 20° to 60°.

5. The method in accordance with claim 4, wherein the angle of inclination is in a range of 30° to 35°.

6. The method in accordance with claim 1, wherein the chemical sterilizing agent flows from the nozzle into a mouth section of the preform.

7. The method in accordance with claim 6, wherein an outlet of the nozzle is positioned closer to an edge of the mouth section than to the longitudinal axis.

8. The method in accordance with claim 6, wherein a discharge zone of the nozzle is positioned at a distance from an edge of the mouth section.

9. A device for sterilizing preforms that are made of a thermoplastic material and are intended for production of blow-molded containers, the device comprising: a heating line for heating an inner surface of the preform to at least 80° C.; a delivery device for applying a chemical sterilizing agent to at least part of the preform, wherein at least one nozzle for discharging the chemical sterilizing agent has a mean discharge direction of the chemical sterilizing agent, the mean direction of discharge having an angle of inclination to a longitudinal axis of the preform, the device further comprising a stationary sterilization device arranged in a region of a blowing machine and operative to discharge the chemical sterilization agent into the preform in an area of the inner surface that was heated to a temperature of at least 80° C., and a device for conveying the preforms past the stationary sterilization device.

10. The device in accordance with claim 9, wherein the angle of inclination is in a range of 10° to 80°.

11. The device in accordance with claim 8, wherein the nozzle has an outlet positioned closer to an edge of a mouth section of the preform than to the longitudinal axis.

12. The device in accordance with claim 11, wherein a discharge zone of the nozzle is positioned at a distance from an edge of the mouth section.

* * * * *